United States Patent
Deremaux et al.

(10) Patent No.: US 8,445,460 B2
(45) Date of Patent: May 21, 2013

(54) SOLUBLE, HIGHLY BRANCHED GLUCOSE POLYMERS FOR ENTERAL AND PARENTERAL NUTRITION AND FOR PERITONEAL DIALYSIS

(75) Inventors: Laëtitia Deremaux, Lille (FR); Carole Petitjean, Marquette Lez Lille (FR); Daniel Wills, Morbecque (FR)

(73) Assignee: Roquette Freres, Lestrem (FR)

( * ) Notice: Subject to any disclaimer, the term of this patent is extended or adjusted under 35 U.S.C. 154(b) by 844 days.

(21) Appl. No.: 12/280,990

(22) PCT Filed: Feb. 15, 2007

(86) PCT No.: PCT/FR2007/000276
§ 371 (c)(1),
(2), (4) Date: Sep. 29, 2008

(87) PCT Pub. No.: WO2007/099212
PCT Pub. Date: Sep. 7, 2007

(65) Prior Publication Data
US 2010/0273735 A1    Oct. 28, 2010

(51) Int. Cl.
| *A61K 31/715* | (2006.01) |
| *A61K 31/716* | (2006.01) |
| *C08B 30/00* | (2006.01) |
| *C08B 30/18* | (2006.01) |
| *C08B 30/20* | (2006.01) |

(52) U.S. Cl.
USPC .......... 514/54; 514/58; 514/778; 514/60; 536/123.1; 536/124; 536/125; 536/102; 536/103

(58) Field of Classification Search
USPC .......... 514/54, 58, 778, 60; 536/123.1, 536/124, 125, 102, 103
See application file for complete search history.

(56) References Cited

U.S. PATENT DOCUMENTS

| 6,630,586 B1 | 10/2003 | Fouache et al. |
| 6,861,519 B2 | 3/2005 | Backer et al. |
| 2005/0159329 A1 | 7/2005 | Fuertes et al. |
| 2007/0202577 A1 | 8/2007 | Sommermeyer |

FOREIGN PATENT DOCUMENTS

| EP | 1 006 128 A1 | 6/2000 |
| EP | 1 369 432 A2 | 12/2003 |
| EP | 1 548 033 A2 | 6/2005 |
| WO | 2005/083103 A1 | 9/2005 |

*Primary Examiner* — Shaojia Anna Jiang
*Assistant Examiner* — Michael C Henry
(74) *Attorney, Agent, or Firm* — Young & Thompson

(57) ABSTRACT

The invention relates to soluble, highly branched glucose polymers which are obtained by enzymatic treatment of starch, having a reducing sugars content of less than 3.5%, exhibiting a proportion of α-1,6-glucosidic linkages of between 20% and 30%, a Mw, determined by light scattering, of between $20 \cdot 10^3$ and $30 \cdot 10^3$ daltons, and an osmolality of less than 25 mOsm/kg. The invention likewise relates to a method of obtaining these polymers and to their use in the pharmaceutical and food industries, more particularly in the field of enteral and parenteral nutrition, and in the field of peritoneal dialysis.

20 Claims, No Drawings

SOLUBLE, HIGHLY BRANCHED GLUCOSE POLYMERS FOR ENTERAL AND PARENTERAL NUTRITION AND FOR PERITONEAL DIALYSIS

The invention relates to soluble, highly branched glucose polymers which are obtained by enzymatic treatment of starch, having a reducing sugars content of less than 3.5%, preferably less than 2.5%, even more preferably less than 1%, and exhibiting a proportion of α-1,6-glucosidic linkages of between 20% and 30%, and a weight-average molecular weight (Mw) chosen within a very narrow range of between $20 \times 10^3$ and less than $30 \times 10^3$ daltons.

The soluble, highly branched glucose polymers of the present invention also exhibit a low osmolality, determined according to a test A, having a value of less than 25 mOsm/kg, preferably between 5 and 20 mOsm/kg.

These polymers may also be hydrogenated or isomerized so as to increase their stability, in particular their thermal stability.

These soluble, highly branched glucose polymers exhibit, moreover, a low viscosity and a lack of retrogradation, even after cold storage for long periods of time.

The invention also relates to a process for producing such soluble, highly branched glucose polymers.

The invention also relates to compositions comprising such soluble, highly branched glucose polymers. These compositions can be used in many industrial applications, in particular in the food and pharmaceutical industries.

The adjective "soluble" used in relation to the glucose polymers of the present invention means that these polymers are water-soluble.

Glucose polymers that are conventionally produced industrially are prepared by hydrolysis of natural or hybrid starches and derivatives thereof.

Conventional starch hydrolysates are thus produced by acid or enzymatic hydrolysis of starch from cereals or from tubers. They are in fact a mixture of glucose and glucose polymers, of extremely varied molecular weights.

These starch hydrolysates (dextrins, maltodextrins, etc.) produced industrially (with a certain degree of polymerization or average DP) comprise a broad distribution of saccharides containing both linear structures (α-1,4-glucosidic linkages) and branched structures (α-1,6-glucosidic linkages).

These starch hydrolysates, and in particular maltodextrins, are generally used as a transporter or a filler, as a texturing agent, as a spray-drying support, as a fat substitute, as a film-forming agent, as a freezing regulator, as an anticrystallizing agent, or as an energy source.

It is known to those skilled in the art that the saccharide composition of maltodextrins determines both their physical and biological properties.

Thus, their hygroscopicity, their fermentability, their viscosity, their sweetening nature, their stability, their gelling nature and their osmolality are criteria which are conventionally assessed and chosen according to the various fields in which they are used.

Basic knowledge of the physicochemical behavior of these saccharides thus leads to their being incorporated, for example, into solutions for peritoneal dialysis, parenteral and enteral fluids, or into foods for diabetics.

As a result, for these various uses, various physical and biological properties are required.

It is, for example, known that the rate of absorption of these saccharides is determined by the rate of gastric emptying and the rate of intestinal adsorption, the regulation of which is provided by the osmolality of said saccharides.

At the intestinal level, the maltodextrins are hydrolyzed by pancreatic α-amylase, which leads to their size being reduced to the limit dextrins, and then a certain number of enzymes bound to the intestinal mucosa, such as maltase, sucrase and α-dextrinase, continue to hydrolyze the linear and branched saccharides to glucose.

While glucose, maltose and maltotriose easily cross the intestinal barrier (passive diffusion), the same is not true of higher oligosaccharides. In addition, linear oligosaccharides are absorbed more rapidly than branched oligosaccharides.

The colonic bacteria will subsequently ferment all the carbohydrates which have not crossed the wall of the small intestine. Excessive fermentation by these bacteria then often leads to intestinal disorders such as cramps and flatulence.

It is also known that the osmolality influences the rate of absorption and of secretion of water in the small intestine. The higher the osmolality of a compound, the more said compound induces entry of fluid into the intestine and leads to intestinal upsets (osmotic diarrhea), with concomitant loss of fluid and of electrolytes.

The osmolality of a solution is defined as the quantity of moles dissolved per kg of water, which implies that, at the same concentration by dry weight, the osmolality of a conventional maltodextrin increases as its DP decreases.

A high osmolality means that the low-molecular-weight substances bind to water, which makes the transport of water and nutrients across the intestinal wall difficult. The osmolality of blood is approximately 300 mOsm/kg, and with the aim of facilitating the transport of nutrients, it is desirable for the osmolality of the substance to be notably below this value.

A dextrin according to WO 95/22562, having an average molecular weight of approximately 720 000 daltons and a degree of branching of approximately 4%, is described as having an osmolality of 20 mOsm/kg.

These dextrins are prepared by acid treatment of natural starch, more particularly of potato flour, under high temperature conditions, i.e. 110 to 140° C. and in a reaction time of 1 to 15 hours, which results in the formation of 1,6-branches which correspond both to α-1,6- and β-1,6-glucosidic linkages.

Atypical β-glucosidic linkages are not hydrolyzed by the enzymatic systems of the intestine, and result in the accumulation of undigestible residues that certain undesirable bacteria of the colon will assimilate.

In the field of parenteral and enteral solutions, nutritive solutions are designed to keep a patient in good health and to provide said patient with nutrients when he or she cannot be fed via the natural digestive routes.

When the solutions are directly provided intravenously, they must be isotonic and the glucose intake is thus limited.

In order to provide a daily energy of 10 000 kJ, it is described, in an article in *Food Science Technology* from 1999, pp 345-355 by Marchal et al., that it would be necessary to infuse 14 liters of isotonic glucose solution (5% weight/volume of glucose), which largely exceeds human capacities.

The intake of more concentrated glucose or fructose solutions (10 to 20% weight/volume) is possible, but not for long periods and provided that the infusion is performed in large vessels, the subclavian vein for example.

It is also possible to administer linear saccharides with a DP of between 2 and 5, since these saccharides are hydrolyzed by maltases in the kidney and the glucose released is then reabsorbed. Accordingly, the use of short linear oligosaccharides makes it possible to provide sufficient energy in an isotonic solution, without overhydrating the patient.

Moreover, since linear oligosaccharides with a DP of less than 7 are stable in solution over long periods of time, it is conventionally chosen to vary the DP between 2 and 7 so as to make it possible to constantly provide patients, over these long periods, with all the energy required.

However, this solution is not entirely satisfactory and it envisions only the use of linear glucosidic structures.

As regards enteral nutrition, it concerns drinks that can be ingested orally or alternatively can be administered via a tube into the stomach or the small intestine.

For these enteral fluids, the major problem is diarrhea, due to too high an osmolality.

Conventionally, to remedy this problem, maltodextrins containing a complex mixture of linear and branched saccharides, with a dextrose equivalent (DE) of 10 to 20, are used. These maltodextrins are not, however, entirely satisfactory.

Specialists in enteral and parenteral nutrition are searching for the solution to these technical problems in the production of branched structures in starch-derived products.

Amylopectin, the principal constituent of starch, is organized around linear α-1,4-linkages and α-1,6-linkages, which constitute branching points. Knowledge of the microstructures has revealed that these two types of linkages are not uniformly distributed, but that in said microstructures zones very dense in α-1,6-linkages border zones comprising only α-1,4-linkages.

It has been proposed, in U.S. Pat. No. 4,840,807, or patent application JP 11/187,708, to extract only the zones dense in α-1,6-linkages, as a source of slowly absorbed carbohydrates, in the sense that the α-1,6-linkages are slower to degrade than the α-1,4-linkages.

Two families of products have thus been developed. The first concerns the limit dextrins prepared by degradation of the α-1,4-linkage zones with an α-amylase alone, and the dextrins prepared by degradation of the α-1,4-linkage zones through the simultaneous action of an α-amylase and of an α-amylase.

The resistance of these limit dextrins to human digestive enzymes makes it possible to use them for regulating digestion, but also for controlling glycemia (use in diabetic nutrition). This effect is attributed to a delay in the speed of intestinal absorption.

However, these compounds have the drawback of having a very low molecular weight, which limits the use thereof in the other fields of use where it is necessary to have products of a certain viscosity.

Patent EP 207,676 teaches that, for use in continuous and ambulatory peritoneal dialysis, starch hydrolysates that form clear and colorless solutions at 10% in water, having an Mw of $5 \times 10^3$ to $1 \times 10^6$ daltons and a low polydispersity index or Ip, are preferred.

This is reflected by compositions which contain predominantly high-molecular-weight glucose polymers of between $5 \times 10^3$ and $5 \times 10^5$ daltons, which contain very little or no glucose or oligosaccharides with a DP of less than or equal to 3, and very little or no glucose polymers of Mw greater than $1 \times 10^6$ daltons.

In fact, for this use, the low-molecular-weight polymers or monomers which rapidly cross the peritoneal wall are of no value for the creation of a long-lasting osmotic pressure gradient, and furthermore, the polymers of very high molecular weight, greater than $1 \times 10^6$ daltons and which are devoid of any osmotic capacity, are to be avoided and even prohibited since there is a risk of them retrograding and precipitating in the organism.

Peritoneal dialysis consists in introducing a dialysis solution into the peritoneal cavity by means of a catheter. After a certain period of time, an exchange of solutes takes place between the blood and the dialysate. The use of an appropriate osmotic agent makes it possible to drain excess water from the blood to the dialysate, and to thus compensate for the deficiency of the kidneys.

The conventional peritoneal dialysis method for removing the excess water (ultrafiltration) and excess solutes from the organism consists in injecting, into the peritoneal cavity, a dialysis solution that is hypertonic with respect to the blood due to the addition of glucose as osmotic agent.

The flow through an ideal semipermeable membrane is principally determined by the total number of solute molecules (osmolality) present in the solution, independently of their size. On the other hand, in the case of a biological membrane such as the peritoneal membrane, the flow depends only on the solutes which do not, or barely, cross the membrane, and is not therefore necessarily linked to the total osmolality of the solution.

In addition, the ability of the solutes to cross the membrane also depends on the shape of the molecules, on their ionic charge and also on their size.

The choice of an ideal osmotic agent is tricky: the latter should enable an osmotic gradient so as to move water and toxic substances from the blood to the dialysis solution through the peritoneum. It should also be nontoxic and biologically inert, while at the same time being metabolizable by the organism, a part of the latter being assimilated in the blood. It should not cross the peritoneal membrane too rapidly, so as to maintain an ultrafiltration gradient over a long period of time, and so as not to allow the accumulation of undegradable, undesirable substances in the blood.

In its patent EP 667,356, the applicant company proposed a method for preparing, from waxy starch, a starch hydrolysate which is completely water-soluble and has a low polydispersity index less than 2.8, and a Mw of between $5 \times 10^3$ and $1 \times 10^6$ daltons.

This process consists in hydrolyzing, via the acid process, a milk of starch consisting exclusively of amylopectin, and then in completing this acid hydrolysis by enzymatic hydrolysis using bacterial α-amylase, and in subjecting this hydrolysate to chromatography on macroporous strong cationic resins in alkali metal or alkaline earth metal form.

This particular starch hydrolysate, also called icodextrin, has a molecular weight of 12 000 to 20 000 daltons. The majority of the glucose units (more than 90%) of the icodextrin are linked by α-1,4-linkages, forming linear chains, with a small fraction of α-1,4-chains which are α-1,6-branched (less than 10%).

The icodextrin allowed a significant decrease in the daily absorption of glucose previously used as osmotic agent in solutions for dialysis, thus providing a real advantage for the treatment of diabetic and/or obese patients for whom the calorie load is a critical factor.

The peritoneal dialysis solutions containing icodextrin as osmotic agent (in particular sold by Baxter Healthcare Corp. under the trade name Extraneal®) are in general used for long daily exchanges (nocturnal in ambulatory continuous peritoneal dialysis and diurnal in automated peritoneal dialysis).

This icodextrin could, however, be further improved if there was an osmotic agent which generated less blood glucose, and the osmotic capacity of which lasted longer, leading to a significant simplification of the dialysis treatment procedure.

In fact, since the dialysate yield would be improved, the frequency at which the dialysis bags would be changed would be lower, which would constitute a definite improvement in the patient's quality of life.

Thus, the ideal carbohydrate in peritoneal dialysis should:
be water-soluble, have a low viscosity, not retrograde, i.e. not form a gel by reorganization of the macromolecules constituting said carbohydrate, induce slow glucose appearance kinetics in the systemic circulation, be hydrolyzed slowly, but be completely degraded by the organism's enzymes at the end of this hydrolysis, exert a long-lasting osmotic pressure.

In fact, in relation to these last two points, the outcome of the osmotic agents administered in solution in the peritoneal cavity in patients suffering from kidney failure is determined by their stability in the peritoneal fluid, the degree to which they are absorbed in the blood stream and their rate of hydrolysis by amylase. Now, the osmotic agents of the prior art all have the drawback of being hydrolyzed too rapidly.

From all the above, the result is that there is therefore a need, that has not been met, to have glucose polymers exhibiting notable properties, in particular in terms of stability and solubility, and which confer, on the products which contain them, a longer lifetime and a controlled digestibility, which makes it possible to use them in particular in the fields of peritoneal dialysis, or of enteral or parenteral nutrition, as a glycemia regulator.

It is to the applicant company's credit to have reconciled all these objectives, reputed up until now to be difficult to reconcile, by imagining and developing, at the expense of a great deal of research, novel soluble, highly branched glucose polymers which are obtained by enzymatic treatment.

The soluble, highly branched glucose polymers in accordance with the invention, having a reducing sugars content of less than 3.5%, preferably less than 2.5%, even more preferably less than 1%, are thus characterized in that they have a proportion of α-1,6-glucosidic linkages which is entirely specific, i.e. between 20% and 30%, for a weight-average molecular weight chosen within a narrow range, of between 20 000 and less than 30 000 daltons.

These polymers exhibit an osmolality, determined according to a test A (described in EP 1 369 432) having a value of less than 25 mOsm/kg, preferably between 5 and 20 mOsm/kg.

As indicated above, the soluble, branched glucose polymers in accordance with the invention have a low reducing sugars content of less than 3.5%, preferably less than 2.5%, even more preferably less than 1%. This reducing sugars content can be adjusted within these ranges according to the needs associated with the use. For example, for the use in intraperitoneal dialysis, it is possible to propose products having a reducing sugars content of up to 3.5%.

The reducing sugars content of the branched glucose polymers in accordance with the invention can be determined by any method known to those skilled in the art, in particular by methods for reducing cuprotartaric liquors or by colorimetric methods with dinitrosalicylic acid.

The proportion of α-1,6-glucosidic linkages of the soluble, branched glucose polymers in accordance with the invention is determined by proton NMR analysis. The degree of branching is then expressed as a percentage, corresponding to the amount of signal from the proton, borne by C1 of an anhydroglucose unit linked to another anhydroglucose unit by an α-1,6-linkage, when a value of 100 has been given to all the signals of the glycosidic protons borne by all the C1s of the glucose residues of said soluble glucose polymers.

Under these conditions, the soluble, highly branched glucose polymers in accordance with the invention exhibit a proportion of α-1,6-linkages of between 20% and 30%.

This content of α-1,6-glucosidic linkages confers on the highly branched glucose polymers in accordance with the invention a particular structure, in terms of degree of branching relative to the starch or to the starch derivative from which they are derived.

This particularly high content of α-1,6-glucosidic linkages makes the highly branched glucose polymers according to the invention difficult to digest, which contributes to it being possible to use them in enteral nutrition as a digestion-regulating agent and as a glycemia-regulating agent, or in all the uses where a slowed digestion providing glucose is desired, in particular in diabetics, in sports persons or in elderly individuals.

They can therefore be effectively proposed to diabetics or to predisposed individuals, as foods, drinks or nutrition supplements, the function of which is to inhibit raised glycemia.

The weight-average molecular weights (Mw) of the glucose polymers of the present invention are measured by size exclusion chromatography (SEC) on PSS Suprema 100 and PSS Suprema 1000 columns mounted in series and coupled to a light scattering detector.

The soluble, highly branched glucose polymers of the invention exhibit a weight-average molecular weight (Mw) of between 20 000 and less than 30 000 daltons, preferably between 20 000 and 28 000, and particularly preferably between 24 000 and 27 000.

These branched glucose polymers in accordance with the invention constitute a new family of polymers, characterized by a particular molecular weight which is quite different than that of the soluble, branched glucose polymers that the applicant company has already described in its patent application EP 1,369,432.

The soluble, branched glucose polymers in accordance with the invention also exhibit a particularly low osmolality.

The measurement of the osmolality of the soluble, branched glucose polymers in accordance with the invention is carried out according to the same test A as that described in patent application EP 1,369,432, and gives an osmolality value of less than 25 mOsm/kg, preferably between 5 and 20 mOsm/kg.

To the applicant company's knowledge, no glucose polymers exist which have such an osmolality value, for a degree of branching and a weight-average molecular weight as indicated above.

Other measurements, carried out on limit dextrins obtained by treatment of liquefied starch with α-amylase, sold under the name BLD 8 by Sanmatsu, exhibit, for a molecular weight of between 40 000 and 50 000 daltons and a degree of α-1,6-branching of between 8% and 9%, an osmolality value of more than 35 mOsm/kg.

The soluble glucose polymers of the present invention are produced by enzymatic treatment of starch. During the production thereof, they in particular do not undergo any treatments capable of introducing atypical glucosidic linkages such as α- and β-1,2, α- and β-1,3, β-1,4 and β-1,6 linkages.

As regards the soluble, branched glucose polymers described by the applicant company in its patent application EP 1,369,432, they admittedly exhibit an osmolality value which does not exceed 15 mOsm/kg, but have a weight-average molecular weight which is higher than that of the polymers of the present invention, between 35 000 and 200 000 daltons.

This osmolality value of less than 25 mOsm/kg, preferably between 5 and 20 mOsm/kg, thus confers on the soluble, highly branched polymers in accordance with the invention, properties which allow them to be advantageously used in the context of enteral and parenteral nutrition.

Their low osmolality and their molecular weight profile make these highly branched glucose polymers in accordance with the invention perfect candidates as osmotic agents for uses in peritoneal dialysis, as will be exemplified hereinafter.

The applicant company has also noted that the soluble, highly branched glucose polymers in accordance with the invention exhibit better resistance to alpha-amylase than the soluble, highly branched glucose polymers of its previous patent application EP 1,369,432. This resistance confers, on the glucose polymers, significant advantages compared with the polymers of the prior art, such as icodextrin. It means that these polymers do not generate as much blood glucose and prolongs the duration of their osmotic capacity in a medium containing alpha-amylase, thus allowing them to be used in dialysis treatments of long duration.

Finally, the soluble, highly branched glucose polymers in accordance with the invention can be advantageously modified chemically or biologically in order to increase their stability, in particular their thermal stability.

Accordingly, these polymers can be hydrogenated so as to give polymers of which the final reducing glucose end is replaced with a nonreducing sorbitol end.

Such a conversion can be obtained in particular by catalytic hydrogenation techniques well-known to those skilled in the art. These techniques consist, for example, in subjecting a solution of a reducing sugar, in the case in point a solution of soluble, highly branched glucose polymers of the invention, in the presence of a Raney nickel catalyst, to a hydrogen pressure of 40 to 70 kg/cm$^2$ and a temperature of 100 to 150° C. The hydrogenation is pursued for several hours until the hydrogenated product shows virtually no more reducing capacity.

The soluble, highly branched glucose polymers according to the invention can also be subjected to the action of enzymes extracted in particular from bacteria of the rhizobium, arthrobacter or sulfolobus genus, which have the particularity of isomerizing the terminal reducing maltose link of the polymers to a nonreducing α-α trehalose link.

Such an isomerization can be obtained, for example, using the techniques described in patent EP 606,753, the teachings of which are incorporated herein by way of reference. It consists in subjecting a solution of soluble, highly branched glucose polymers to the action of an enzyme forming nonreducing saccharides at a temperature of 40 to 55° C. and a pH of between 5 and 10.

It should be noted here that neither of these two processes, hydrogenation or enzymatic isomerization, substantially modifies the products subjected to these actions.

The soluble, branched glucose polymers of the present invention can be prepared according to a process comprising the succession of the following steps:
1) preparing an aqueous solution of waxy starch, having a solids content of from 10% to 30% by weight,
2) treating said solution successively with 2 to 3 ml of a branching enzyme at 30 000-50 000 U/ml per 100 g of waxy starch, at a temperature of between 60° C. and 80° C. for a period of 18 to 24 hours, and then with a saccharification enzyme chosen from amyloglucosidase or α-amylase, preferably amyloglucosidase,
3) fractionating the solution obtained in such a way as to eliminate the low-molecular-weight fractions, preferably those having a molecular weight of less than 9000, and to recover the other fractions, i.e. the high-molecular-weight fractions,
4) recovering the highly branched glucose polymers thus obtained.

The starch used in the process claimed is a waxy starch, in other words an amylopectin-rich starch.

It is, however, possible to obtain the soluble glucose polymers of the present invention by applying the above process to starches other than waxy starches. In general, said starches may be chosen from natural or hybrid starch derived from potato, from potato with a high amylopectin content (waxy potato flour), from pea, from rice, from cassava, from wheat, from corn, from amylopectin-rich corn or wheat (waxy corn or wheat), from corn with a high amylose content, from cuts or fractions that can be made or obtained from starches, such as amylose, amylopectin, the particle-size cuts known to those skilled in the art as wheat starch "A" and wheat starch "B", and mixtures of the abovementioned products.

The starch derivatives can be taken to mean modified starches derived from the enzymatic, chemical and/or physical modification, in one or more steps, of this starch.

The starch derivatives may in particular be starches modified by means of at least one of the known techniques of etherification, esterification, crosslinking, oxidation, alkaline treatment, acid hydrolysis and/or enzymatic hydrolysis (responsible for maltodextrins and dextrins).

The applicant company has found that the highly branched glucose polymers in accordance with the invention can be readily synthesized from starches, or from derivatives thereof, which already exhibit a degree of branching at least equal to 1%.

The preparation of the highly branched glucose polymers in accordance with the invention is carried out by modifying the operating conditions already described in patent application EP 1,269,432 by the applicant company.

In patent application EP 1,369,432, the applicant company recommended using from 50 000 to 500 000 U of purified branching enzyme per 100 g, on a dry weight basis, of starch or of starch derivative, at a temperature of between 25 and 95° C., preferably at a temperature of between 70 and 95° C., for a period of 18 to 24 hours.

The term "branching enzyme" is intended to mean the branching enzymes chosen from the group consisting of glycogen-branching enzymes, starch-branching enzymes and any mixtures of these enzymes.

To obtain the novel highly branched glucose polymers in accordance with the invention, the applicant company recommends preferably treating the starch solution, preferably waxy starch solution, with from 2 to 3 ml of branching enzyme at 30 000-50 000 U/ml per 100 g of starch, at a temperature of between 60 and 80° C. for a period of 18 to 24 hours.

The second step of the process in accordance with the invention also consists in bringing a saccharification enzyme, such as amyloglucosidase or α-amylase, preferably amyloglucosidase, to act on the waxy starch solution pretreated with the branching enzyme.

For amyloglucosidase, for example, the reaction conditions (temperature and pH) are the following: from 0.15 to 0.25 ml of amyloglucosidase, for example of Dextrozyme W type from Novozymes at 270 AGU/g or of Optidex type from Solvay Enzymes at 300 AGU/g per 100 g of starch, at a temperature of 60° C., and a pH of 4 to 5, for 1 to 3 hours, preferably for 2 hours.

After this treatment, the soluble, highly branched glucose polymers of the invention are obtained as a mixture with their enzymatic degradation products, predominantly consisting of glucose, maltose and isomaltose.

The third step of the process consists in carrying out a fractionation using a known technique chosen, for example, from the group of membrane separations and chromatography, so as to recover the high-molecular-weight fractions and to remove the low-molecular-weight fractions, as described in patent application EP 1,369,432 by the applicant company.

Whatever the method used, the profiles obtained make it possible to separate the high-molecular-weight polysaccharide fraction corresponding to the soluble, highly branched glucose polymers in accordance with the invention, from the low-molecular-weight oligosaccharide fractions produced by the hydrolysis and having a molecular mass of less than 1000 daltons, consisting essentially of glucose, maltose and isomaltose.

The final step of the process in accordance with the invention therefore consists in collecting the fractions of molecular weight between 20 000 and less than 30 000 daltons corresponding to the highly branched glucose polymers.

These fractions can be combined as they are, the polymers can be precipitated by adding ethanol, purified and dried under vacuum or else by atomization, by any technique known to those skilled in the art.

The particular physicochemical characteristics of the polymers of the present invention allow them to be used in the food, pharmacy, cosmetology and dermatology industries, and even more particularly in pharmacy, in the enteral and parenteral nutrition fields, in the glycemia regulation field, in the peritoneal dialysis field as an osmotic agent, and as a blood plasma substitute.

A subject of the present invention is therefore also compositions containing the highly branched glucose polymers described above. These compositions are in particular intended to be used in humans or animals in food and pharmaceutical applications.

This composition may be in solid form for extemporaneous preparation, in liquid form, for example in an aqueous solution, or in concentrated form intended to be diluted with water or with any other suitable diluent.

A subject of the invention is also the use of such compositions in enteral and parenteral nutrition and as a glycemia-regulating agent.

As regards the particular field of peritoneal dialysis, the applicant company has found, by means of an alpha-amylase-resistance test, that the polymers in accordance with the invention are particularly suitable for the preparation of solutions for peritoneal dialysis, as is subsequently exemplified, where these polymers are used as an osmotic agent.

It should be noted that the applicant company has thus overcome a technical prejudice according to which, as is asserted in particular in International patent application WO 2004/022602, the starch-based products that can be used in peritoneal dialysis should exhibit a degree of α-1,6-branching of preferably between 11% and 18% and a molecular weight of between 10 000 and 200 000.

A subject of the invention is also a solution for peritoneal dialysis, characterized in that it comprises, as osmotic agent, at least one soluble, highly branched glucose polymer which is obtained by enzymatic treatment of starch, having
   a reducing sugars content of less than 3.5%,
   a proportion of α-1,6-glucosidic linkages of between 20% and 30%,
   a weight-average molecular weight (Mw), determined by light scattering, of between 20 000 and less than 30 000 daltons.

In such a solution for peritoneal dialysis, the soluble, highly branched glucose polymer having a reducing sugars content of less than 3.5%, preferably has
   a proportion of α-1,6-glucosidic linkages of between 20% and 25%,
   a weight-average molecular weight (MW), determined by light scattering, having a value of between 24 000 and 27 000 daltons.

The solution for peritoneal dialysis according to the invention may also comprise physiologically acceptable electrolytes, such as sodium, potassium, calcium, magnesium or chlorine, so as to prevent the loss by transfer of electrolytes from the serum to the peritoneum.

When the solution is obtained by dissolving the highly branched polymers according to the invention in water, it should be clear and colorless. It is preferably free of endotoxins, of peptidoglucans and of beta-glucans, and also of contaminants originating from the starting material or from the enzymatic preparations used to produce it.

To this effect, the highly branched polymers used in said solution will preferably have undergone purification so as to remove any coloration or any unwanted contaminant such as proteins, bacteria, bacterial toxins, fiber, traces of metals, etc.

This purification step can be carried out according to the techniques known to those skilled in the art.

The solution for dialysis according to the invention may also comprise buffering agents (lactate, acetate, gluconate in particular) and other additives such as amino acids, insulin, polyols such as, for example, sorbitol, erythritol, mannitol, maltitol or xylitol, or hydrogenated starch hydrolysates.

The addition of polyols to the composition, and preferably of apyrogenic polyols free of the impurities described above (endotoxins and other residues of bacterial origin in particular), makes it possible to increase the osmolality of the solution more advantageously than with glucose or maltose, owing to their greater osmotic capacity and because they are not reducing.

Finally, it is also possible to complete the dialysis solution containing the soluble, highly branched glucose polymers of the invention with glucose, maltose and/or glucose polymers.

Amino-acid-based solutions for peritoneal dialysis are of definite value in the prevention of accelerated aging of the peritoneum associated with glucose and its derivatives, even though their cost and the risk of a tricky regulation of acidosis limits the exclusive and continuous prescription thereof.

It is therefore possible to envision making up a mixture of various molecules in the same solution for peritoneal dialysis: glucose, soluble, highly branched glucose polymers in accordance with the invention, and amino acids.

It is then preferred to sterilize these various constituents separately (use of compartmentalized bags), in order to avoid in particular the generation of glucose degradation products (GDPs) or products resulting from the binding of glucose to said amino acids (AGES) responsible for harmful effects on the stability of the peritoneal membrane.

The solution for dialysis according to the invention is, moreover, advantageous compared with the products of the prior art, since the osmotic agent that it contains makes it possible to exert a long-lasting osmotic pressure and induces slow glucose appearance kinetics, while at the same time being stable to retrogradation, thus meeting the principal criteria defined above.

Other characteristics and advantages of the invention will emerge on reading the nonlimiting examples described below.

EXAMPLE 1

A starch milk is prepared from an acid-fluidified waxy corn starch with a fluidity level WF of approximately 90, sold by the applicant company under the trade mark Cleargum® CB 90.

For this, a suspension of starch containing 25% solids is prepared with stirring, the pH being adjusted to 7.5.

Complete solubilization of the starch is carried out in a continuous cooker at 145° C. for 3 to 4 minutes. The solution is then cooled to 70° C. and the glycogen-branching enzyme purified from *Bacillus stearothermophilus* (according to a protocol known, moreover, to those skilled in the art) is added continuously at a rate of 2.5 ml of enzyme solution at 40 000 U/ml per 100 g, on a dry weight basis, of substrate.

The enzymatic reaction is carried out for 20 hours at 70° C. and at pH 7, and then stopped by heating at 90° C. for 1 h.

The complementary treatment with 0.20 ml of amyloglucosidase (Dextrozyme W from Novozymes at 270 AGU/g) per 100 g, on a dry weight basis, of starch is carried out in the preceding reaction medium, brought to a temperature of 60° C. and to a pH of 4.3.

The incubation is carried out for 2 hours, and the reaction is stopped by heating at 90° C. for 1 h.

The solution is then purified by treatment on active carbon in a proportion of 2% com/dry of Norit SX+, at pH 5 for 1 h, and then filtered.

The final solution is then fractionated by ultrafiltration through a membrane with a cutoff threshold of 9000 daltons (ES209 membrane from PCI), and the retentate is collected and atomized.

Table I below gives the results of the physicochemical characteristics of the soluble, branched glucose polymer in accordance with the invention thus obtained.

TABLE I

| | |
|---|---|
| Proportion of α-1,6-linkages (%) | 22.9 |
| Mw ($10^3$ daltons) | 25 |
| Reducing sugars content (Bertrand assay (%)) | 2.3 |
| Glucose (%) | 0.6 |
| Osmolality (mOsm/kg) | 18 |

EXAMPLE 2

This example refers to a test carried out under semi-industrial conditions.

In a 1.5 $m^3$ tank, 175 kg of Cleargum® CB 90 are mixed with water so as to reach a solids content of 13%. The pH is adjusted to 7.

Complete solubilization of the starch is carried out in a semi-industrial continuous cooker at approximately 150° C. for a few minutes at a flow rate of 400 kg/h. The solution is then cooled continuously to 70° C. and the glycogen-branching enzyme purified from *Bacillus stearothermophilus* is added continuously at a rate of 2.5 ml of enzyme solution at 40 000 U/ml per 100 g, on a dry weight basis, of substrate.

The enzymatic reaction is carried out for 20 hours at 70° C. and at pH 7 in a stirred tank, and then stopped by heating at 90° C. for 1 h.

The complementary treatment with 0.18 ml of amyloglucosidase (Optidex from Solvay Enzymes at 300 AGU/g) per 100 g, on a dry weight basis, of starch is carried out in the preceding reaction medium, brought to a temperature of 60° C. and to a pH of 4.3.

The incubation is carried out for 2 hours, and the reaction is stopped by heating at 90° C. for 1 h.

The solution is then purified by treatment with active carbon in a proportion of 2% com/dry of Norit SX+, at pH 5 for 1 h, and then filtered.

The final solution is then fractionated by ultrafiltration through a membrane with a cutoff threshold of 9000 daltons (ES209 membrane from PCI).

The solution derived from the ultrafiltration treatment is then purified by demineralization followed by a further treatment with active carbon in a proportion of 2% com/dry of Norit SX+.

The final solution is subsequently filtered and then atomized under standard conditions known to those skilled in the art.

Table I below gives the results of the physicochemical characteristics of the soluble, branched glucose polymer in accordance with the invention thus obtained.

TABLE I

| | |
|---|---|
| Proportion of α-1,6-linkages (%) | 22 |
| Mw ($10^3$ daltons) | 29.8 |
| Reducing sugars content (Bertrand assay (%)) | 0.6 |
| Glucose (%) | <0.01 |
| Osmolality (mOsm/kg) | 8 |

EXAMPLE 3

Aqueous solutions of highly branched polymers in accordance with the invention, obtained according to Example 1, are prepared and are brought into contact with an amylase of pancreatic origin in order to simulate the hydrolysis of products in the peritoneum.

The progression over time of the amylase hydrolysis is followed by measuring the reducing sugars formed and the glucose which appears in the reaction medium.

This test makes it possible to evaluate the resistance of the polymers to amylase hydrolysis, which is an essential criterion in the choice of an osmotic agent for a dialysis solution.

The polymer of Example 1 is tested in comparison with icodextrin (osmotic agent of the prior art).

Other polymers, prepared by the applicant company according to the teaching of its patent EP 1,369,432, are also tested by way of comparison.

They are the products "a" and "b" as prepared in accordance with Example 3 and the product Z as prepared in accordance with Example 2 of said patent application EP 1,369,432.

The icodextrin is prepared in accordance with patent EP 667,356 mentioned in the description.

A maltose control is carried out in order to validate the in vitro model of enzymatic digestion.

The operating conditions for the amylase digestion are the following:

weigh out precisely 0.6 g of test product,
add 150 ml of Na maleate buffer, pH 7, at 0.1 mol/l,
stir until complete dissolution of the product,
place the flasks in a water bath for 15 minutes, so that the temperature of the solution is 37° C.,
take a sample of 1.5 ml at time 0 minute (sample SI),
add 0.15 g of porcine pancreatin (α-amylase of animal origin),
incubate at 37° C. in a thermostated water bath with stirring for 300 minutes,
take samples of 1.5 ml at times: 15, 30, 45, 60, 90, 120, 180, 240, 300 minutes,
stop the enzymatic reaction by placing the samples in a dry bath at 100° C., for 10 minutes, assay the glucose on the samples, so as to simulate the impact on glycemia of the product studied, assay the reducing sugars on the samples in order to study the rate of hydrolysis.

For the glucose assay, a colorimetric method is used, carried out on a Hitachi 704 automated device (Roche). The reagent used is a reagent containing the GOD/PAP (glucose oxidase, peroxidase) enzymes.

The volume of reagent used is 500 microliters, the sample volume is 5 microliters and the reaction temperature is 30° C.

The method used for assaying the reducing sugars is the Somogyi Nelson method. 200 microliters of sample are placed in a stoppered tube, and 200 microliters of working solution (sodium tartrate and copper sulfate reagents) are added.

The mixture is brought to boiling, and, after cooling, arsenomolybdic reagent is added, followed by water.

The solution obtained is deposited in a microplate, and then the absorbance is read in a microplate reader at a wavelength of 520 nanometers.

The results are given in the following tables:

1. Glucose appearance kinetics (as % released on a dry weight basis)

| Time (min) | Maltose | Polymer according to the invention | "a" | "b" | Z | Icodextrin |
|---|---|---|---|---|---|---|
| SI | 0.26 | 0.36 | 3.35 | 0.00 | 0.53 | 0.28 |
| 15 | 0.79 | 1.79 | 5.31 | 1.59 | — | 3.07 |
| 30 | 1.06 | 1.91 | 5.68 | 1.96 | 2.11 | 3.63 |
| 45 | 1.59 | 2.21 | 5.86 | 2.24 | — | 3.91 |
| 60 | 2.12 | 2.12 | 6.14 | 2.52 | 2.37 | 4.19 |
| 90 | 2.65 | 2.43 | 6.52 | 2.89 | — | 4.75 |
| 120 | 3.44 | 2.63 | 6.61 | 3.17 | 2.90 | 5.31 |
| 180 | 5.03 | 3.21 | 7.26 | 4.76 | 3.43 | 6.15 |
| 240 | 6.35 | 3.62 | 8.10 | — | 3.96 | 6.99 |
| 300 | 7.68 | 4.01 | 8.38 | 5.41 | 4.22 | 7.82 |

2. Reducing sugar appearance kinetics (as % on a dry weight basis)

| Time (min) | Maltose | Polymer according to the invention | "a" | "b" | Z | Icodextrin |
|---|---|---|---|---|---|---|
| SI | 51.01 | 2.25 | 5.76 | 0.88 | 1.45 | 2.74 |
| 15 | 47.94 | 10.20 | 19.33 | 18.96 | — | 30.39 |
| 30 | 48.29 | 9.53 | 20.00 | 19.04 | 11.00 | 32.53 |
| 45 | 48.55 | 11.93 | 20.25 | 19.78 | — | 32.46 |
| 60 | 48.84 | 11.42 | 19.92 | 20.80 | 11.10 | 32.95 |
| 90 | 49.42 | 11.29 | 20.37 | 19.42 | — | 34.16 |
| 120 | 47.15 | 10.23 | 21.68 | 21.04 | 12.16 | 34.40 |
| 180 | 48.87 | 13.04 | 22.46 | 21.79 | 12.22 | 36.64 |
| 240 | 50.90 | 12.60 | 23.05 | 23.11 | 12.29 | 37.03 |
| 300 | 52.20 | 13.66 | 22.67 | 22.88 | 13.64 | 37.06 |

3. Summary of results

| PRODUCTS TESTED | % glucose released at 300 min. | % reducing sugars formed at 300 min. | Proportion of α-1,6-linkages as % | Molar mass (daltons) |
|---|---|---|---|---|
| Maltose | 7.68 | 52.20 | 0 | 342 |
| Icodextrin | 7.82 | 37.06 | 6.5-8 | 12 000-20 000 |
| Polymer in accordance with the invention | 4.01 | 13.66 | 22.9 | 25 000 |
| "a" | 8.38 | 22.67 | 19.4 | 33 000 |
| "b" | 5.41 | 22.88 | 14.3 | 68 000 |
| z | 4.22 | 13.64 | 24.2 | 45 000 |

According to the results obtained with the compounds "a", "b" and Z, the applicant company, in its patent application EP 1,369,432 already deduced therefrom that the higher the degree of branching (the proportion of α-1,6-linkages), the less the amylase hydrolysis. The latter is also dependent on the molecular weight. Thus, the higher the degree of branching and the lower the molecular weight, the less the molecule is attacked by the amylase.

While the soluble, branched glucose polymer according to the invention confirms this tendency, it should, however, be noted that, although having a degree of α-1,6 branching that is lower than the compound Z, and a molecular weight that is virtually half that of the compound Z, it is characterized by a degree of hydrolysis that is equivalent to, or even slightly less than, that of said compound Z.

The soluble, branched glucose polymer of the invention therefore constitutes the best compromise in terms of molecular weight, branched structure and behavior as regards its amylase resistance.

Moreover, compared with icodextrin, which is a reference compound as an osmotic agent in peritoneal dialysis, the soluble glucose polymers in accordance with the invention constitute an improved variant thereof, since they exhibit a resistance to hydrolysis by pancreatic amylase that is clearly greater than that of icodextrin.

This means especially that the product of the present invention shows a definite advantage in terms of blood-glucose-generating capacity, for a molecular weight very close to icodextrin.

In order to confirm this observation, the applicant company undertook a study aimed at comparing the ability of these two compounds to exert a long-lasting osmotic capacity, by determining the distribution of the molar masses of the product after the action of pancreatic α-amylase.

It is in fact well known to those skilled in the art that the more a compound is rapidly hydrolyzed to small molecules, the less it will be able to exert a long-lasting osmotic capacity in peritoneal dialysis.

The following table reflects the molar mass distribution of icodextrin and of the soluble, branched glucose polymer in accordance with the invention, the molar masses being measured after digestion with α-amylase. This distribution is expressed as % of products of which the molecular weight is greater than 1000 daltons.

|  | % of molar masses > 1000 daltons |
| --- | --- |
| Icodextrin | 37.8 |
| Polymer in accordance with the invention | 88 |

It therefore appears that approximately 62% of the icodextrin was hydrolyzed to molecules of less than 1000 daltons after 300 min of amylase digestion, whereas only 22% was hydrolyzed for the soluble glucose polymer in accordance with the invention.

At equivalent molecular weight, the soluble, branched glucose polymer in accordance with the invention therefore exhibits a much better behavior than icodextrin, and constitutes a very advantageous product for use in peritoneal dialysis.

The invention claimed is:

1. A soluble, highly branched glucose polymer which is obtained by enzymatic treatment of starch, having a reducing sugars content of less than 3.5%, characterized in that it exhibits:
    a proportion of α-1,6-glucosidic linkages of between 20% and 30%,
    a weight-average molecular weight (Mw), determined by light scattering, of between 20 000 and less than 30 000 daltons.

2. The polymer as claimed in claim 1, characterized in that it exhibits an osmolality, determined according to a test A, having a value of less than 25 mOsm/kg, preferably between 5 and 20 mOsm/kg.

3. The polymer as claimed in claim 1, characterized in that it is enzymatically isomerized so that its reducing ends are converted to trehalose, or in that it is hydrogenated.

4. A food or pharmaceutical product for humans or animals, characterized in that it contains the highly branched glucose polymer as claimed in claim 1.

5. A solution for peritoneal dialysis, characterized in that it comprises, as osmotic agent, at least one soluble, highly branched polymer as claimed in claim 1.

6. The solution for dialysis as claimed in claim 5, characterized in that the soluble, highly branched polymer having a reducing sugars content of less than 3.5% exhibits:
    a proportion of α-1,6-glucosidic linkages of between 20% and 25%,
    a weight-average molecular weight (Mw), determined by light scattering, of between 24 000 and 27 000 daltons.

7. The solution for peritoneal dialysis as claimed in claim 5, characterized in that it also comprises a polyol chosen from the group consisting of sorbitol, mannitol, maltitol, xylitol, erythritol and hydrogenated starch hydrolysates.

8. The solution for peritoneal dialysis as claimed in claim 7, characterized in that it also comprises buffering agents.

9. The solution for peritoneal dialysis as claimed in claim 5, characterized in that it also comprises glucose, maltose and/or glucose polymers.

10. The solution for peritoneal dialysis as claimed in claim 5, characterized in that it also comprises amino acids and glucose.

11. The polymer as claimed in claim 2, characterized in that it is enzymatically isomerized so that its reducing ends are converted to trehalose, or in that it is hydrogenated.

12. A food or pharmaceutical product for humans or animals, characterized in that it contains the highly branched glucose polymer as claimed in claim 2.

13. A food or pharmaceutical product for humans or animals, characterized in that it contains the highly branched glucose polymer as claimed in claim 3.

14. The solution for peritoneal dialysis as claimed in claim 6, characterized in that it also comprises a polyol chosen from the group consisting of sorbitol, mannitol, maltitol, xylitol, erythritol and hydrogenated starch hydrolysates.

15. The solution for peritoneal dialysis as claimed in claim 6, characterized in that it also comprises glucose, maltose and/or glucose polymers.

16. The solution for peritoneal dialysis as claimed in claim 6, characterized in that it also comprises amino acids and glucose.

17. The polymer as claimed in claim 1, characterized in that it has a reducing sugars content of less than 2.5%.

18. The polymer as claimed in claim 1, characterized in that it has a reducing sugars content of less than 1%.

19. A method for feeding a patient in need of nutrients that the patient cannot be fed via natural digestives routes, comprising the step of administering enterally or parenterally the composition as claimed in claim 4 to the patient.

20. A method for providing a slowed digestion delivering glucose in a patient in need thereof, comprising the step of administering the composition as claimed in claim 4 to the patient.

* * * * *

UNITED STATES PATENT AND TRADEMARK OFFICE
CERTIFICATE OF CORRECTION

PATENT NO.       : 8,445,460 B2                                          Page 1 of 1
APPLICATION NO.  : 12/280990
DATED            : May 21, 2013
INVENTOR(S)      : Deremaux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 977 days.

Signed and Sealed this
Eighth Day of September, 2015

Michelle K. Lee
*Director of the United States Patent and Trademark Office*